United States Patent
Miller et al.

(10) Patent No.: US 10,973,803 B2
(45) Date of Patent: Apr. 13, 2021

(54) SODIUM SALT OF N-((1,2,3,5,6,7-HEXAHYDRO-S-INDACEN-4-YL)CARBAMOYL)-1-ISOPROPYL-1H-PYRAZOLE-3-SULFONAMIDE

(71) Applicant: INFLAZOME LIMITED, Dublin (IE)

(72) Inventors: David Miller, Cambridge (GB); Angus Macleod, Cambridge (GB); Susana Del Rio Gancedo, Cambridge (GB); Samuel Alexander Stratford, Cambridge (GB)

(73) Assignee: Inflazome Limited, Dublin (IE)

( * ) Notice: Subject to any disclaimer, the term of this patent is extended or adjusted under 35 U.S.C. 154(b) by 0 days.

(21) Appl. No.: 16/850,978

(22) Filed: Apr. 16, 2020

(65) Prior Publication Data

US 2020/0237723 A1   Jul. 30, 2020

Related U.S. Application Data

(63) Continuation of application No. PCT/EP2019/060311, filed on Apr. 23, 2019.

(30) Foreign Application Priority Data

Apr. 23, 2018 (GB) .................................... 1806578

(51) Int. Cl.
*A61K 31/415* (2006.01)

(52) U.S. Cl.
CPC ........ *A61K 31/415* (2013.01); *C07B 2200/13* (2013.01)

(58) Field of Classification Search
None
See application file for complete search history.

(56) References Cited

U.S. PATENT DOCUMENTS

| 10,538,487 B2 | 1/2020 | O'Neill et al. |
| 2019/0359564 A1 | 11/2019 | O'Neill et al. |

FOREIGN PATENT DOCUMENTS

| WO | WO 2016/131098 A1 | 8/2016 |
| WO | WO 2019/206871 A1 | 10/2019 |
| WO | WO 2020/079207 A1 | 4/2020 |

OTHER PUBLICATIONS

WO Application No. PCT/EP2019/060311 PCT International Search Report and Written Opinion of the International Searching Authority dated Oct. 7, 2019.

*Primary Examiner* — Samantha L Shterengarts
(74) *Attorney, Agent, or Firm* — Alston & Bird LLP

(57) ABSTRACT

The present invention relates to a sodium salt of N-((1,2,3,5,6,7-hexahydro-s-indacen-4-yl)carbamoyl)-1-isopropyl-1H-pyrazole-3-sulfonamide and to hydrates, solvates and polymorphic forms thereof. The present invention further relates to pharmaceutical compositions comprising this compound and the use of this compound in the treatment and prevention of medical disorders and diseases, most especially by NLRP3 inhibition.

32 Claims, 4 Drawing Sheets

SODIUM SALT OF N-((1,2,3,5,6,7-HEXAHYDRO-S-INDACEN-4-YL)-CARBAMOYL)-1-ISOPROPYL-1H-PYRAZOLE-3-SULFONAMIDE

CROSS-REFERENCE TO RELATED APPLICATION

This application is a continuation of PCT/EP2019/060311 filed Apr. 23, 2019, incorporated by reference in its entirety for all purposes, which claims priority to GB 1806578.9 filed Apr. 23, 2018.

FIELD OF THE INVENTION

The present invention relates to a sodium salt of N-((1,2,3,5,6,7-hexahydro-s-indacen-4-yl)carbamoyl)-1-isopropyl-1H-pyrazole-3-sulfonamide and to hydrates, solvates and polymorphic forms thereof. The present invention further relates to pharmaceutical compositions comprising this compound and the use of this compound in the treatment and prevention of medical disorders and diseases, most especially by NLRP3 inhibition.

BACKGROUND OF THE INVENTION

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1 and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γ6 T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3$^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1 and WO 2018/015445 A1). WO 2016/131098 A1 discloses N-((1,2,3,5,6,7-hexahydro-s-indacen-4-yl)carbamoyl)-1-isopropyl-1H-pyrazole-3-sulfonamide.

There is a need to provide compounds with improved pharmacological and/or physiological and/or physicochemical properties and/or those that provide a useful alternative to known compounds.

SUMMARY OF THE INVENTION

A first aspect of the present invention provides a sodium salt of N-((1,2,3,5,6,7-hexahydro-s-indacen-4-yl)carbamoyl)-1-isopropyl-1H-pyrazole-3-sulfonamide, or a hydrate or solvate thereof.

A second aspect of the present invention provides a polymorphic form of a sodium salt of N-((1,2,3,5,6,7-hexahydro-s-indacen-4-yl)carbamoyl)-1-isopropyl-1H-pyrazole-3-sulfonamide, or a hydrate or solvate thereof.

In certain embodiments, the polymorphic form of the second aspect is a polymorph of N-((1,2,3,5,6,7-hexahydro-s-indacen-4-yl)carbamoyl)-1-isopropyl-1H-pyrazole-3-sulfonamide monosodium salt monohydrate. Examples of such polymorphs include the polymorph referred to herein as Form 1.

In certain embodiments, the polymorphic form of the second aspect is a polymorph of N-((1,2,3,5,6,7-hexahydro-s-indacen-4-yl)carbamoyl)-1-isopropyl-1H-pyrazole-3-sulfonamide monosodium salt anhydrate. Examples of such polymorphs include the polymorph referred to herein as Form 2.

A third aspect of the present invention provides a process for preparing a sodium salt of N-((1,2,3,5,6,7-hexahydro-s-indacen-4-yl)carbamoyl)-1-isopropyl-1H-pyrazole-3-sulfonamide, comprising:
(a) contacting N-((1,2,3,5,6,7-hexahydro-s-indacen-4-yl)carbamoyl)-1-isopropyl-1H-pyrazole-3-sulfonamide free acid and a source of sodium ions in the presence of one or more polar solvents to form a mixture; and
(b) obtaining a solid sodium salt of N-((1,2,3,5,6,7-hexahydro-s-indacen-4-yl)carbamoyl)-1-isopropyl-1H-pyrazole-3-sulfonamide from the mixture.

A fourth aspect of the present invention provides a pharmaceutical composition comprising a salt, hydrate or solvate of the first aspect of the invention or a polymorphic form of the second aspect of the invention, and a pharmaceutically acceptable excipient.

Further aspects of the present invention provide medical uses and methods of treatment or prevention of a disease, disorder or condition, most especially by NLRP3 inhibition.

DETAILED DESCRIPTION OF THE INVENTION

Figure 1:
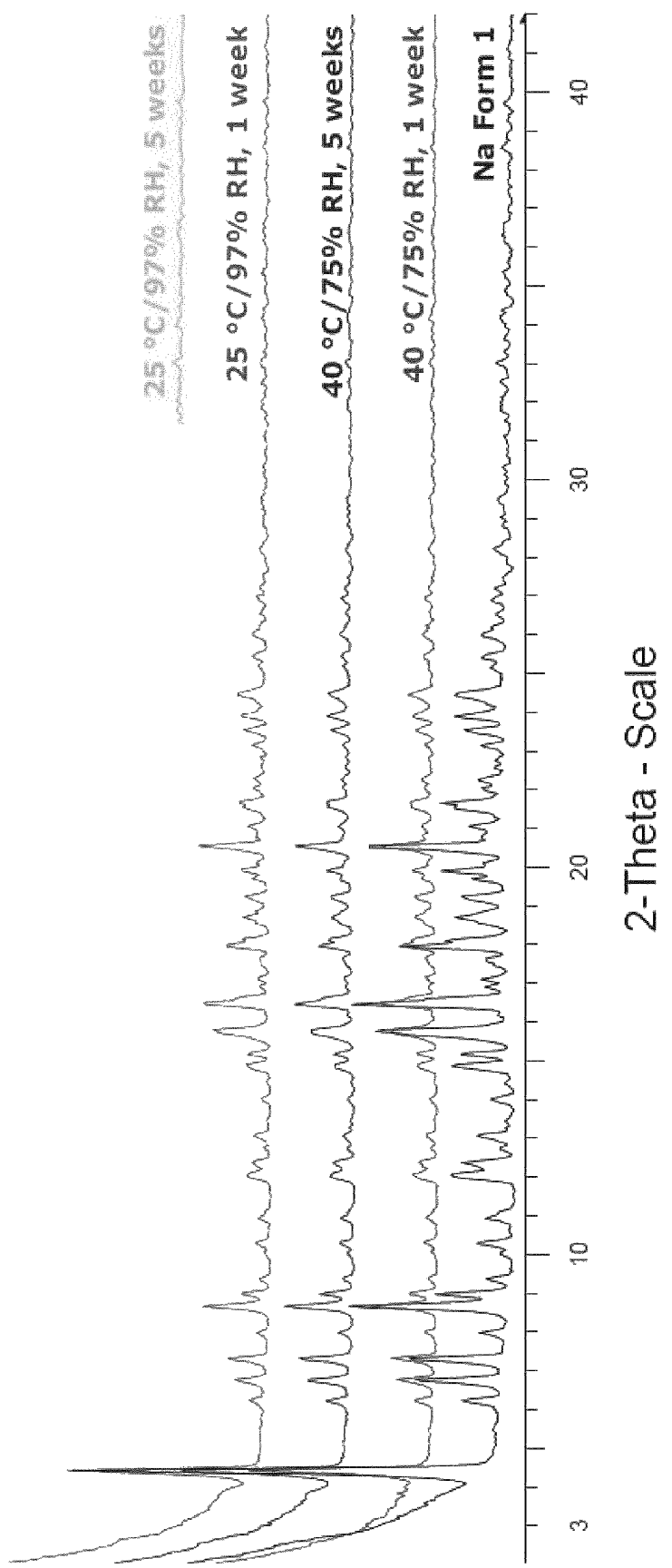
FIG. 1 shows XRPD analysis of the salt of Example 2.

Differences between salt forms of an active pharmaceutical compound can have profound effects on the properties of the solid form of the compound. For example, differences can arise in the crystallinity, solubility, intrinsic dissolution rate, stability under storage, and stability in aqueous media of the solid form of a substance as compared to the non-salified compound and other salt forms of the same compound.

The salts of the present invention provide forms of N-((1,2,3,5,6,7-hexahydro-s-indacen-4-yl)carbamoyl)-1-isopropyl-1H-pyrazole-3-sulfonamide, and in particular sodium salts, which have certain advantages over other salts and over the free acid itself.

A first aspect of the present invention provides a sodium salt of N-((1,2,3,5,6,7-hexahydro-s-indacen-4-yl)carbamoyl)-1-isopropyl-1H-pyrazole-3-sulfonamide, or a hydrate or solvate thereof. N-((1,2,3,5,6,7-Hexahydro-s-indacen-4-yl)carbamoyl)-1-isopropyl-1H-pyrazole-3-sulfonamide (also referred to as the free acid) has the formula:

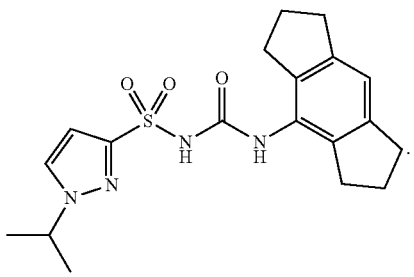 [SMILES: CC(C)n1ccc(S(=O)(=O)NC(=O)Nc2c3c(cc4c2CCC4)CCC3)n1]

The salts of the first aspect of the present invention encompass salts having any ratio of the conjugate base of the free acid to sodium ion, for example monosodium salts, disodium salts and hemisodium salts. In one embodiment, the sodium salt of N-((1,2,3,5,6,7-hexahydro-s-indacen-4-yl)carbamoyl)-1-isopropyl-1H-pyrazole-3-sulfonamide is a monosodium salt.

The salts of the first aspect of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol. In one embodiment, the sodium salt of N-((1,2,3,5,6,7-hexahydro-s-indacen-4-yl)carbamoyl)-1-isopropyl-1H-pyrazole-3-sulfonamide is a monohydrate or anhydrate. In one embodiment, the sodium salt of N-((1,2,3,5,6,7-hexahydro-s-indacen-4-yl)carbamoyl)-1-isopropyl-1H-pyrazole-3-sulfonamide is a monohydrate.

The salts, hydrates and solvates of the first aspect of the invention may be in any crystalline or amorphous form or may exist as any mixture of crystalline and amorphous forms. In embodiments where a salt, hydrate and/or solvate of the first aspect of the invention exists as a mixture of crystalline and amorphous forms, the salt, hydrate and/or solvate may have a degree of crystallinity. As used herein the degree of crystallinity is the weight percentage of the salt, hydrate and/or solvate of the first aspect of the invention which is in one or more crystalline forms, expressed as a percentage of the total weight of the salt, hydrate and/or solvate.

The salts, hydrates and solvates of the first aspect of the invention preferably have a degree of crystallinity of 50% or more (e.g. 60% or more, 70% or more, 80% or more, 90% or more, 95% or more, or 99% or more). More preferably, the salts, hydrates and solvates of the first aspect of the invention are crystalline. As used herein a salt, hydrate and/or solvate of the first aspect of the invention is typically referred to as crystalline, if it has a degree of crystallinity 90% or more (e.g. 95% or more, or 99% or more).

In one embodiment, the sodium salt of N-((1,2,3,5,6,7-hexahydro-s-indacen-4-yl)carbamoyl)-1-isopropyl-1H-pyrazole-3-sulfonamide is crystalline. In one embodiment, the sodium salt of N-((1,2,3,5,6,7-hexahydro-s-indacen-4-yl)carbamoyl)-1-isopropyl-1H-pyrazole-3-sulfonamide is a crystalline monosodium salt of N-((1,2,3,5,6,7-hexahydro-s-indacen-4-yl)carbamoyl)-1-isopropyl-1H-pyrazole-3-sulfonamide monohydrate.

A crystalline salt, hydrate and/or solvate of the first aspect of the invention may exist in one or more polymorphic forms. Polymorphism refers to the ability of a solid substance to exist in one or more distinct crystal structures (i.e. with one or more distinct arrangements of molecules relative to each other in the crystal lattice). Different polymorphs of a substance may have different physical properties such as solubility, intrinsic dissolution rate and calorimetric behaviour (e.g. melting point). Different polymorphs may also exhibit differences in stability (e.g. differences in stability with respect to conversion to other crystalline or amorphous forms). The physical properties of an active pharmaceutical ingredient may affect the drug product safety performance and efficacy. It is therefore advantageous to identify polymorphic forms of a drug substance which have pharmaceutically acceptable properties.

Accordingly, a second aspect of the present invention provides a polymorphic form of a sodium salt of N-((1,2,3,5,6,7-hexahydro-s-indacen-4-yl)carbamoyl)-1-isopropyl-1H-pyrazole-3-sulfonamide, or a hydrate or solvate thereof.

The salts, hydrates and solvates of the first aspect of the invention and the polymorphic forms of the second aspect of the invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

In certain embodiments, the polymorphic form of the second aspect is a polymorph of N-((1,2,3,5,6,7-hexahydro-s-indacen-4-yl)carbamoyl)-1-isopropyl-1H-pyrazole-3-sulfonamide monosodium salt monohydrate. Examples of such polymorphs include the polymorph referred to herein as Form 1.

The Form 1 polymorph can be characterised by techniques including X-Ray Powder Diffraction (XRPD), Differential Scanning Calorimetry (DSC) and/or Thermogravimetric Analysis (TGA).

As used herein, XRPD data are typically those which can be obtained using CuKα radiation at 20° C. As used herein, the term "approximate" or "approximately" when used in connection with the position of an XRPD peak typically refers to the stated position ±0.2° 2θ.

The Form 1 polymorph typically has an XRPD spectrum comprising peaks at approximately: 4.3° 2θ, 8.7° 2θ, and 20.6° 2θ. More typically, the Form 1 polymorph has an XRPD spectrum comprising peaks at approximately: 4.3° 2θ, 7.3° 2θ, 8.7° 2θ, 16.5° 2θ, and 20.6°×2θ. Still more typically, the Form 1 polymorph has an XRPD spectrum comprising peaks at approximately: 4.3° 2θ, 6.7° 2θ, 7.3° 2θ, 8.7° 2θ, 15.8° 2θ, 16.5° 2θ, and 20.6° 2θ. Still further typically, the Form 1 polymorph has an XRPD spectrum comprising peaks at approximately: 4.3° 2θ, 6.7° 2θ, 7.3° 2θ, 8.7° 2θ, 9.0° 2θ, 15.8° 2θ, 16.5° 2θ, 18.0° 2θ, and 20.6° 2θ.

The Form 1 polymorph typically has an XRPD spectrum in which the 10 most intense peaks include 5 or more (e.g. 6 or more, 7 or more, 8 or more, 9 or more, or 10) peaks which have an approximate 2θ value selected from: 4.3° 2θ, 6.2° 2θ, 6.7° 2θ, 7.3° 2θ, 8.7° 2θ, 9.0° 2θ, 12.1° 2θ, 15.8° 2θ, 16.5° 2θ, 18.0° 2θ, 18.1° 2θ, 20.6° 2θ, 21.6° 2θ, and 24.5° 2θ. More typically, the Form 1 polymorph has an XRPD spectrum in which the 10 most intense peaks include 5 or more (e.g. 6 or more, 7 or more, 8 or more, 9 or more, or 10) peaks which have an approximate 2θ value selected from: 4.3° 2θ, 6.2° 2θ, 6.7° 2θ, 7.3° 2θ, 8.7° 2θ, 9.0° 2θ, 12.1° 2θ, 15.8° 2θ, 16.5° 2θ, 18.0° 2θ, 20.6° 2θ, and 21.6° 2θ. Still more typically, the Form 1 polymorph has an XRPD spectrum in which the 10 most intense peaks include 5 or more (e.g. 6 or more, 7 or more, 8 or more, 9 or more, or 10) peaks which have an approximate 2θ value selected from: 4.3° 2θ, 6.2° 2θ, 6.7° 2θ, 7.3° 2θ, 8.7° 2θ, 9.0° 2θ, 15.8° 2θ, 16.5° 2θ, 18.0° 2θ, and 20.6° 2θ.

The Form 1 polymorph may have an XRPD spectrum approximately as set out in Table 1 below:

TABLE 1

| Form 1 | |
|---|---|
| Angle/° 2θ | Intensity % |
| 4.3 | 100.0 |
| 6.2 | 25.4 |
| 6.7 | 38.7 |
| 7.3 | 42.0 |
| 8.0 | 16.0 |
| 8.7 | 51.1 |
| 9.0 | 29.8 |
| 9.4 | 13.2 |
| 10.0 | 9.2 |
| 10.3 | 15.3 |
| 10.6 | 6.5 |
| 10.9 | 15.4 |
| 12.1 | 22.5 |
| 12.3 | 18.8 |
| 12.7 | 8.6 |
| 13.0 | 10.6 |
| 13.4 | 6.3 |
| 14.0 | 8.3 |
| 14.9 | 16.9 |
| 15.2 | 16.3 |
| 15.8 | 36.5 |
| 16.5 | 41.8 |
| 17.1 | 11.8 |
| 17.6 | 12.1 |
| 18.0 | 26.4 |
| 18.1 | 21.8 |
| 18.7 | 19.9 |
| 19.2 | 19.1 |
| 19.7 | 16.0 |
| 19.9 | 20.8 |
| 20.6 | 42.2 |
| 21.1 | 13.8 |
| 21.6 | 23.4 |
| 22.0 | 11.7 |
| 22.3 | 12.8 |
| 22.8 | 8.9 |
| 23.2 | 10.4 |
| 23.6 | 16.3 |
| 24.0 | 21.3 |
| 24.5 | 21.6 |
| 25.1 | 10.3 |
| 25.4 | 12.7 |
| 26.0 | 12.7 |
| 26.9 | 10.4 |
| 27.3 | 9.8 |

The Form 1 polymorph typically has a TGA profile comprising weight loss of about 4.6% to about 5.0% (e.g. weight loss of about 4.7% to about 4.9%, or weight loss of about 4.8%) between 20° C. and 100° C.

The Form 1 polymorph typically has a DSC profile comprising a first endotherm and a second endotherm. The first endotherm of the Form 1 polymorph typically has an onset at a temperature in a range from about 41° C. to about 45° C. (e.g. a temperature in a range from about 42° C. to about 44° C., or at a temperature of about 43° C.). The first endotherm of the Form 1 polymorph typically has a peak at a temperature in a range from about 72° C. to about 76° C. (e.g. a temperature in a range from about 73° C. to about 75° C., or at a temperature of about 74° C.). The first endotherm of the Form 1 polymorph typically has an enthalpy change of about 69 J/g to about 73 J/g (e.g. about 70 J/g to about 72 J/g, or about 71 J/g). The second endotherm of the Form 1 polymorph typically has an onset at a temperature in a range from about 177° C. to about 181° C. (e.g. a temperature in a range from about 178° C. to about 180° C., or at a temperature of about 179° C.). The second endotherm of the Form 1 polymorph typically has a peak at a temperature in a range from about 188° C. to about 192° C. (e.g. a temperature in a range from about 189° C. to about 191° C., or at a temperature of about 190° C.). The second endotherm of the Form 1 polymorph typically has an enthalpy change of about 13 J/g to about 17 J/g (e.g. about 14 J/g to about 16 J/g, or about 15 J/g).

The Form 1 polymorph can be obtained by a process comprising:
(a) contacting N-((1,2,3,5,6,7-hexahydro-s-indacen-4-yl) carbamoyl)-1-isopropyl-1H-pyrazole-3-sulfonamide free acid and a source of sodium ions in the presence of water and optionally a polar aprotic organic solvent to form a solution; or dissolving N-((1,2,3,5,6,7-hexahydro-s-indacen-4-yl)carbamoyl)-1-isopropyl-1H-pyrazole-3-sulfonamide monosodium salt in a solvent mixture comprising water and optionally a polar aprotic organic solvent to form a solution; and
(b) obtaining a crystalline monosodium salt of N-((1,2,3,5, 6,7-hexahydro-s-indacen-4-yl)carbamoyl)-1-isopropyl-1H-pyrazole-3-sulfonamide monohydrate as the Form 1 polymorph from the solution.

In a preferred embodiment, the solvent mixture used in step (a) comprises water and a polar aprotic organic solvent. In a preferred embodiment, the polar aprotic organic solvent is acetone. The volume ratio of water to polar aprotic organic solvent is typically from 1:35 to 1:1 (e.g. from 1:20 to 1:1, or from 1:15 to 1:4, or from 1:13 to 1:6, or from 1:11 to 1:8, or about 1:9). In a preferred embodiment, N-((1,2,3,5,6,7-hexahydro-s-indacen-4-yl)carbamoyl)-1-isopropyl-1H-pyrazole-3-sulfonamide free acid is treated with a solvent mixture of water and a polar aprotic organic solvent, followed by addition of a source of sodium ions to form a solution.

In a preferred embodiment, in step (b), the crystalline monosodium salt of N-((1,2,3,5,6,7-hexahydro-s-indacen-4-yl)carbamoyl)-1-isopropyl-1H-pyrazole-3-sulfonamide monohydrate Form 1 polymorph may be obtained from the solution by addition of a suitable antisolvent, or by a combination of addition of a suitable antisolvent and addition of seed crystals. Preferred antisolvents are diethyl ether, diisopropyl ether and tert-butyl methyl ether. Particularly preferred is tert-butyl methyl ether.

Further preferred processes for obtaining the Form 1 polymorph include those in which the polar aprotic organic solvent, source of sodium ions, means of obtaining the solid sodium salt and other features of the process are as described herein with respect to the process of the third aspect of the present invention.

In certain embodiments, the polymorphic form of the second aspect is a polymorph of N-((1,2,3,5,6,7-hexahydro-s-indacen-4-yl)carbamoyl)-1-isopropyl-1H-pyrazole-3-sulfonamide monosodium salt anhydrate. Examples of such polymorphs include the polymorph referred to herein as Form 2.

The Form 2 polymorph typically has an XRPD spectrum comprising peaks at approximately: 5.1° 2θ, 21.7° 2θ, and 22.7° 2θ. More typically, the Form 2 polymorph has an XRPD spectrum comprising peaks at approximately: 5.1° 2θ, 17.9° 2θ, 18.7° 2θ, 21.7° 2θ, and 22.7° 2θ. Still more typically, the Form 2 polymorph has an XRPD spectrum comprising peaks at approximately: 5.1° 2θ, 17.1° 2θ, 17.9° 2θ, 18.7° 2θ, 20.1° 2θ, 21.7° 2θ, and 22.7° 2θ. Still further typically, the Form 2 polymorph has an XRPD spectrum comprising peaks at approximately: 5.1° 2θ, 8.9° 2θ, 17.1° 2θ, 17.9° 2θ, 18.7° 2θ, 20.1° 2θ, 20.6° 2θ, 21.7° 2θ, and 22.7° 2θ.

The Form 2 polymorph typically has an XRPD spectrum in which the 10 most intense peaks include 5 or more (e.g. 6 or more, 7 or more, 8 or more, 9 or more, or 10) peaks which have an approximate 2θ value selected from: 5.1° 2θ, 6.6° 2θ, 7.7° 2θ, 8.9° 2θ, 9.3° 2θ, 10.3° 2θ, 16.2° 2θ, 17.1° 2θ, 17.9° 2θ, 18.7° 2θ, 20.1° 2θ, 20.6° 2θ, 21.7° 2θ, and 22.7° 2θ. More typically, the Form 2 polymorph has an XRPD spectrum in which the 10 most intense peaks include 5 or more (e.g. 6 or more, 7 or more, 8 or more, 9 or more, or 10) peaks which have an approximate 2θ value selected from: 5.1° 2θ, 6.6° 2θ, 8.9° 2θ, 10.3° 2θ, 16.2° 2θ, 17.1° 2θ, 17.9° 2θ, 18.7° 2θ, 20.1° 2θ, 20.6° 2θ, 21.7° 2θ, and 22.7° 2θ. Still more typically, the Form 2 polymorph has an XRPD spectrum in which the 10 most intense peaks include 5 or more (e.g. 6 or more, 7 or more, 8 or more, 9 or more, or 10) peaks which have an approximate 2θ value selected from: 5.1° 2θ, 8.9° 2θ, 16.2° 2θ, 17.1° 2θ, 17.9° 2θ, 18.7° 2θ, 20.1° 2θ, 20.6020, 21.7° 2θ, and 22.7° 2θ.

The Form 2 polymorph may have an XRPD spectrum approximately as set out in Table 2 below:

TABLE 2

| Form 2 | |
|---|---|
| Angle/° 2θ | Intensity % |
| 5.1 | 100.0 |
| 6.6 | 15.3 |
| 7.7 | 15.0 |
| 8.9 | 19.1 |
| 9.3 | 15.0 |
| 10.3 | 15.1 |
| 11.0 | 10.3 |
| 11.9 | 10.5 |
| 13.2 | 10.1 |
| 13.9 | 11.5 |
| 14.7 | 11.4 |
| 16.2 | 15.7 |
| 17.1 | 20.6 |
| 17.9 | 22.5 |
| 18.7 | 21.8 |
| 20.1 | 21.1 |
| 20.6 | 20.4 |
| 21.7 | 22.6 |
| 22.7 | 23.3 |

The Form 2 polymorph typically has a TGA profile comprising weight loss of about 8.5% to about 8.9% (e.g. weight loss of about 8.6% to about 8.8%, or weight loss of about 8.7%) between 20° C. and 160° C.

The Form 2 polymorph typically has a DSC profile comprising a first endotherm, a second endotherm and a third endotherm. The first endotherm of the Form 2 polymorph typically has an onset at a temperature in a range from about 61° C. to about 65° C. (e.g. a temperature in a range from about 62° C. to about 64° C., or at a temperature of about 63° C.). The first endotherm of the Form 2 polymorph typically has a peak at a temperature in a range from about 73° C. to about 77° C. (e.g. a temperature in a range from about 74° C. to about 76° C., or at a temperature of about 75° C.). The first endotherm of the Form 2 polymorph typically has an enthalpy change of about 1 J/g to about 5 J/g (e.g. about 2 J/g to about 4 J/g, or about 3 J/g). The second endotherm of the Form 2 polymorph typically has an onset at a temperature in a range from about 93° C. to about 97° C. (e.g. a temperature in a range from about 94° C. to about 96° C., or at a temperature of about 95° C.). The second endotherm of the Form 2 polymorph typically has a peak at a temperature in a range from about 99° C. to about 103° C. (e.g. a temperature in a range from about 100° C. to about 102° C., or at a temperature of about 101° C.). The second endotherm of the Form 2 polymorph typically has an enthalpy change of about 0.5 J/g to about 4 J/g (e.g. about 1 J/g to about 3 J/g, or about 2 J/g). The third endotherm of the Form 2 polymorph typically has an onset at a temperature in a range from about 180° C. to about 184° C. (e.g. a temperature in a range from about 181° C. to about 183° C., or at a temperature of about 182° C.). The third endotherm of the Form 2 polymorph typically has a peak at a temperature in a range from about 196° C. to about 200° C. (e.g. a temperature in a range from about 197° C. to about 199° C., or at a temperature of about 198° C.). The third endotherm of the Form 2 polymorph typically has an enthalpy change of about 25 J/g to about 29 J/g (e.g. about 26 J/g to about 28 J/g, or about 27 J/g).

The Form 2 polymorph can be obtained by a process comprising:
(a) contacting N-((1,2,3,5,6,7-hexahydro-s-indacen-4-yl) carbamoyl)-1-isopropyl-1H-pyrazole-3-sulfonamide free acid and a source of sodium ions in the presence of water and a polar protic organic solvent to form a solution; or dissolving N-((1,2,3,5,6,7-hexahydro-s-indacen-4-yl)carbamoyl)-1-isopropyl-1H-pyrazole-3-sulfonamide monosodium salt in a solvent mixture comprising water and a polar protic organic solvent to form a solution; and
(b) obtaining a crystalline monosodium salt of N-((1,2,3,5,6,7-hexahydro-s-indacen-4-yl)carbamoyl)-1-isopropyl-1H-pyrazole-3-sulfonamide anhydrate as the Form 2 polymorph from the solution.

In a preferred embodiment, in step (a), N-((1,2,3,5,6,7-hexahydro-s-indacen-4-yl)carbamoyl)-1-isopropyl-1H-pyrazole-3-sulfonamide monosodium salt is dissolved in a solvent mixture comprising water and a polar protic organic solvent to form a solution.

In a preferred embodiment, the polar protic organic solvent used in step (a) is isopropyl alcohol. The volume ratio of water to polar protic organic solvent is typically from 1:35 to 1:1 (e.g. from 1:20 to 1:1, or from 1:15 to 1:4, or from 1:13 to 1:6, or from 1:11 to 1:8, or about 1:10).

Further preferred processes for obtaining the Form 2 polymorph include those in which the polar protic organic solvent, source of sodium ions, means of obtaining the solid sodium salt and other features of the process are as described herein with respect to the process of the third aspect of the present invention.

A third aspect of the present invention provides a process for preparing a salt, hydrate or solvate of the first aspect of the invention or a polymorphic form of the second aspect of the invention, the process comprising:
(a) contacting N-((1,2,3,5,6,7-hexahydro-s-indacen-4-yl) carbamoyl)-1-isopropyl-1H-pyrazole-3-sulfonamide free acid and a source of sodium ions in the presence of one or more polar solvents to form a mixture; and
(b) obtaining a solid sodium salt of N-((1,2,3,5,6,7-hexahydro-s-indacen-4-yl)carbamoyl)-1-isopropyl-1H-pyrazole-3-sulfonamide from the mixture.

In certain embodiments, the one or more polar solvents used in step (a) are a mixture of polar solvents, e.g. a mixture of water and a polar organic solvent. In such embodiments, the volume ratio of water to polar organic solvent is typically from 1:35 to 1:1 (e.g. from 1:20 to 1:1, or from 1:15 to 1:4, or from 1:13 to 1:6, or from 1:11 to 1:8, or about 1:10, or about 1:9).

The mixture of polar solvents may be, for example, a mixture of water and a polar protic organic solvent, or a mixture of water and a polar aprotic organic solvent. Suitable polar protic organic solvents include acids such as formic acid and acetic acid, and alcohols such as methanol, ethanol, isopropyl alcohol and n-butanol. A preferred polar protic organic solvent is isopropyl alcohol. Suitable polar aprotic organic solvents include N-methylpyrrolidone, tetrahydrofuran, 2-methyltetrahydrofuran, ethyl acetate, methyl acetate, acetone, dimethylformamide, acetonitrile, dimethyl sulfoxide and propylene carbonate. A preferred polar aprotic organic solvent is acetone.

In some embodiments, the mixture of polar solvents may be a mixture of water and isopropyl alcohol. In some embodiments, the mixture of polar solvents may be a mixture of water and acetone.

The source of sodium ions is typically a sodium salt. In some embodiments, the sodium salt is a solid sodium salt. In other embodiments, the sodium salt is a solution of a sodium-ion containing compound. Suitable solid sodium salts include NaCl, NaOH, $Na_2CO_3$ and $NaHCO_3$. Suitable solutions of sodium-ion containing compounds include sodium methoxide (NaOMe), sodium ethoxide (NaOEt) and sodium tert-butoxide (NaO$^t$Bu) all in ethanol, tetrahydrofuran, or acetone or a mixture of any of these solvents with water. Other suitable solutions of sodium-ion containing compounds include NaCl, NaOH, $Na_2CO_3$ and $NaHCO_3$ in water. A preferred source of sodium ions is sodium ethoxide (NaOEt) in ethanol or NaOH in water. A more preferred source of sodium ions is sodium ethoxide (NaOEt) in ethanol.

In some embodiments, in step (a), the reaction mixture formed is a solution. In some embodiments, in step (a), N-((1,2,3,5,6,7-hexahydro-s-indacen-4-yl)carbamoyl)-1-isopropyl-1H-pyrazole-3-sulfonamide free acid is treated with a polar solvent or a mixture of polar solvents, followed by addition of a source of sodium ions to form a solution.

In some embodiments, step (a) is carried out at a temperature in the range of 5° C. to 100° C., or a range of 10° C. to 60° C., or a range of 15° C. to 30° C.

In some embodiments, in step (b), the solid sodium salt of N-((1,2,3,5,6,7-hexahydro-s-indacen-4-yl)carbamoyl)-1-isopropyl-1H-pyrazole-3-sulfonamide may be obtained from the reaction mixture by evaporation of the solvent or mixture of solvents. In some embodiments, the solid sodium salt of N-((1,2,3,5,6,7-hexahydro-s-indacen-4-yl)carbamoyl)-1-isopropyl-1H-pyrazole-3-sulfonamide may be obtained from the reaction mixture by addition of a suitable antisolvent. In such embodiments, the volume ratio of solvent or mixture of solvents to antisolvent is typically from 1:1 to 1:10 (e.g. from 1:1.5 to 1:8, or from 1:2 to 1:6, or about 1:3, or about 1:5). In some embodiments, the solid sodium salt of N-((1,2,3,5,6,7-hexahydro-s-indacen-4-yl) carbamoyl)-1-isopropyl-1H-pyrazole-3-sulfonamide may be obtained from the reaction mixture by addition of seed crystals. In some embodiments, the solid sodium salt of N-((1,2,3,5,6,7-hexahydro-s-indacen-4-yl)carbamoyl)-1-isopropyl-1H-pyrazole-3-sulfonamide may be obtained from the reaction mixture by a combination of addition of a suitable antisolvent and addition of seed crystals.

Suitable antisolvents include non-polar solvents such as hexane, heptane, cyclohexane, toluene, benzene, 1,4-dioxane, chloroform, dichloromethane, diethyl ether, diisopropyl ether and tert-butyl methyl ether. Diethyl ether, diisopropyl ether and tert-butyl methyl ether are preferred. Particularly preferred is tert-butyl methyl ether.

In some embodiments, step (b) is carried out at a temperature in the range of 5° C. to 100° C., or a range of 10° C. to 60° C., or a range of 15° C. to 30° C.

A fourth aspect of the present invention provides a pharmaceutical composition comprising a salt, hydrate or solvate of the first aspect of the invention or a polymorphic form of the second aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a salt, hydrate or solvate of the first aspect of the invention, a polymorphic form of the second aspect of the invention, or a pharmaceutical composition of the fourth aspect of the invention, for use in medicine, and/or for use in the treatment or prevention of a disease, disorder or condition. Typically, the use comprises the administration of the salt, hydrate, solvate, polymorphic form or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a salt, hydrate, solvate, polymorphic form or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant (p≤0.05) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers.

Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a salt, hydrate or solvate of the first aspect of the invention or a polymorphic form of the second aspect of the invention, in the manufacture of a medicament for the treatment or prevention of a disease, disorder or condition. Typically, the treatment or prevention comprises the administration of the salt, hydrate, solvate, polymorphic form or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a salt, hydrate or solvate of the first aspect of the invention, a polymorphic form of the second aspect of the invention, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a salt, hydrate or solvate of the first aspect of the invention, a polymorphic form of the second aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the salt, hydrate, solvate, polymorphic form or pharmaceutical composition to the individual. In one embodiment, the use comprises the co-administration of one or more further active agents. The use may also comprise the diagnosis of an individual having a germline or somatic non-silent mutation in NLRP3, wherein the salt, hydrate, solvate, polymorphic form or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a salt, hydrate or solvate of the first aspect of the invention or a polymorphic form of the second aspect of the invention, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the salt, hydrate, solvate, polymorphic form or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the salt, hydrate, solvate, polymorphic form or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a salt, hydrate or solvate of the first aspect of the invention, a polymorphic form of the second aspect of the invention, or a pharmaceutical composition of the fourth aspect of the invention, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (TID), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 139: 11-18, Coll et al. Nat. Med. 2015 21(3):248-55; and Scott et al. Clin. Exp. Rheumatol 2016 34(1): 88-93), systemic lupus erythematosus (Lu et al. J Immunol. 2017 198(3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017 196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1β has also been suggested in atherosclerosis, myocardial infarction (van Hout et al. Eur. Heart J. 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012 149(4): 847-59), diabetic retinopathy (Loukovaara et al. Acta Ophthalmol. 2017; 95(8): 803-808) and optic nerve damage (Puyang et al. Sci Rep. 2016 Feb. 19; 6:20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): e0122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25):2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13: 1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:
(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;
(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, auto- immune hepatitis, autoimmune oophoritis, autoimmune polyglandular failure, autoimmune thyroiditis, Coeliac disease, Crohn's disease, type 1 diabetes (TID), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behçet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;
(iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;
(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacte-*

*rium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from schistosoma, roundworms, tapeworms or flukes) and prion infections;
(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;
(vi) metabolic diseases such as type 2 diabetes (T2D), atherosclerosis, obesity, gout, and pseudo-gout;
(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;
(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;
(ix) liver diseases including non-alcoholic fatty liver disease (NAFLD) and non-alcoholic steatohepatitis (NASH) including advanced fibrosis stages F3 and F4, alcoholic fatty liver disease (AFLD), and alcoholic steatohepatitis (ASH);
(x) renal diseases including chronic kidney disease, oxalate nephropathy, nephrocalcinosis, glomerulonephritis, and diabetic nephropathy;
(xi) ocular diseases including those of the ocular epithelium, age-related macular degeneration (AMD) (dry and wet), uveitis, corneal infection, diabetic retinopathy, optic nerve damage, dry eye, and glaucoma;
(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;
(xiii) lymphatic conditions such as lymphangitis and Castleman's disease;
(xiv) psychological disorders such as depression and psychological stress;
(xv) graft versus host disease;
(xvi) allodynia including mechanical allodynia; and
(xvii) any disease where an individual has been determined to carry a germline or somatic non-silent mutation in NLRP3.

In one embodiment, the disease, disorder or condition is selected from:
(i) cancer;
(ii) an infection;
(iii) a central nervous system disease;
(iv) a cardiovascular disease;
(v) a liver disease;
(vi) an ocular disease; or
(vii) a skin disease.

More typically, the disease, disorder or condition is selected from:
(i) cancer;
(ii) an infection;
(iii) a central nervous system disease; or
(iv) a cardiovascular disease.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:
(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;
(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);
(iii) a muscular condition such as polymyositis or myasthenia gravis;
(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(vi) a vascular condition such as atherosclerosis, Behcet's disease, vasculitides, or wegener's granulomatosis;

(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium* intracellulare, *Pneumocystis carinii* pneumonia, orchitis/epidydimitis, *legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;

(xvi) a burn, wound, trauma, haemorrhage or stroke;

(xvii) radiation exposure; and/or (xviii) obesity; and/or (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

An eleventh aspect of the invention provides a method of inhibiting NLRP3, the method comprising the use of a salt, hydrate or solvate of the first aspect of the invention, a polymorphic form of the second aspect of the invention, or a pharmaceutical composition of the fourth aspect of the invention, to inhibit NLRP3.

In one embodiment of the eleventh aspect of the present invention, the method comprises the use of a salt, hydrate or solvate of the first aspect of the invention, a polymorphic form of the second aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a salt, hydrate or solvate of the first aspect of the invention, a polymorphic form of the second aspect of the invention, or a pharmaceutical composition of the fourth aspect of the invention, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the salt, hydrate, solvate, polymorphic form or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a salt, hydrate or solvate of the first aspect of the invention, a polymorphic form of the second aspect of the invention, or a pharmaceutical composition of the fourth aspect of the invention, for use in the inhibition of NLRP3. Typically, the use comprises the administration of the salt, hydrate, solvate, polymorphic form or pharmaceutical composition to a subject. In one embodiment, the salt, hydrate, solvate, polymorphic form or pharmaceutical composition is co-administered with one or more further active agents.

A thirteenth aspect of the invention provides the use of a salt, hydrate or solvate of the first aspect of the invention or a polymorphic form of the second aspect of the invention, in the manufacture of a medicament for the inhibition of NLRP3. Typically, the inhibition comprises the administration of the salt, hydrate, solvate, polymorphic form or medicament to a subject. In one embodiment, the salt, hydrate, solvate, polymorphic form or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the salt, hydrate or solvate of the first aspect of the invention, the polymorphic form of the second aspect of the invention, or the pharmaceutical composition of the fourth aspect of the invention. Where the one or more further active agents are administered simultaneously with the salt, hydrate, solvate, polymorphic form or pharmaceutical composition of the present invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
(i) chemotherapeutic agents;
(ii) antibodies;
(iii) alkylating agents;
(iv) anti-metabolites;
(v) anti-angiogenic agents;
(vi) plant alkaloids and/or terpenoids;
(vii) topoisomerase inhibitors;
(viii) mTOR inhibitors;
(ix) stilbenoids;
(x) STING agonists;
(xi) cancer vaccines;
(xii) immunomodulatory agents;
(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulfonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a vinca alkaloid, a podophyllotoxin and/or a taxane. In some embodiments, the one or more vinca alkaloids may be derived from the Madagascar periwinkle, Catharanthus roseus (formerly known as Vinca rosea), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —$N_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CDG60, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDRool (PD1), BMS-986016, MGA271, lirilumab, IPH2201, emactuzumab, INCB024360, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the salt, hydrate, solvate, polymorphic form or pharmaceutical composition of the invention.

For oral administration, the salt, hydrate, solvate, polymorphic form or pharmaceutical composition of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the salt, hydrate, solvate or polymorphic form of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The salt, hydrate, solvate, polymorphic form or pharmaceutical composition of the invention may also be presented as a liposome formulation.

For ocular administration, the salt, hydrate, solvate or polymorphic form of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the salt, hydrate, solvate or polymorphic form of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the salt, hydrate, solvate, polymorphic form or pharmaceutical composition of the invention will generally be provided in the form of ointments, cataplasms (poultices), pastes, powders, dressings, creams, plasters or patches.

Suitable suspensions and solutions can be used in inhalers for airway (aerosol) administration.

The dose of the salt, hydrate, solvate or polymorphic form of the present invention will, of course, vary with the disease, disorder or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES

All solvents, reagents and compounds were purchased and used without further purification unless stated otherwise.

X-Ray Powder Diffraction (XRPD), Ion Chromatography (IC), Karl Fischer titration (KF), Thermogravimetric Analysis (TGA), Differential Scanning Calorimetry (DSC) and high performance liquid chromatography (HPLC) techniques referred to in the examples were carried out under the following conditions: XRPD diffractograms were collected on a Bruker D8 diffractometer using CuKα radiation (40 kV, 40 mA) and a θ-2θ goniometer fitted with a Ge monochromator. The incident beam passed through a 2.0 mm divergence slit followed by a 0.2 mm antiscatter slit and knife edge. The diffracted beam passed through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions as flat plate specimens using powder as received. The sample was prepared on a polished, zero-background (510) silicon wafer by gently pressing onto the flat surface or packed into a cut cavity.

The sample was rotated in its own plane. The details of the s data collection method used are:

Angular range: 2 to 42° 2θ

Step size: 0.05° 2θ

Collection time: 0.5 s/step (total collection time: 6.40 min)

IC data were collected on a Metrohm 930 Compact IC Flex with 858 Professional autosampler and 800 Dosino dosage unit monitor, using IC MagicNet software.

Accurately weighed samples were prepared as stock solutions in a suitable solvent. Quantification was achieved by comparison with standard solutions of known concentration of the ion being analysed. Analyses were performed in duplicate and an average of the values is given unless otherwise stated.

| IC method for cation chromatography | |
|---|---|
| Parameter | Value |
| Type of method | Cation exchange |
| Column | Metrosep C 4-250 (4.0 × 250 mm) |
| Column Temperature (° C.) | Ambient |
| Injection (μl) | Various |
| Detection | Conductivity detector |
| Flow Rate (ml/min) | 0.9 |
| Eluent | 1.7 mM nitric acid |
| | 0.7 mM dipicolinic acid in a 5% acetone aqueous solution |

| IC method for anion chromatography | |
|---|---|
| Parameter | Value |
| Type of method | Anion exchange |
| Column | Metrosep A Supp 5-150 (4.0 × 150 mm) |
| Column Temperature (° C.) | Ambient |
| Injection (μl) | Various |
| Detection | Conductivity detector |
| Flow Rate (ml/min) | 0.7 |
| Eluent | 3.2 mM sodium carbonate |
| | 1.0 mM sodium hydrogen carbonate in a 5% acetone aqueous solution |

KF analysis was carried out on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

TGA data were collected on a TA Instruments Discovery TGA, equipped with a 25 position auto-sampler. Typically, 5-10 mg of each sample was loaded onto a pre-tared aluminium DSC pan and heated at 10° C./min from ambient temperature to 350° C. A nitrogen purge at 25 ml/min was maintained over the sample. The instrument control software was TRIOS and the data were analysed using TRIOS or Universal Analysis.

DSC data were collected on a TA Instruments Q2000 equipped with a 50 position auto-sampler. Typically, 0.5-3 mg of each sample, in a pin-holed aluminium pan, was heated at 10° C./min from 25° C. to 300° C. A purge of dry nitrogen at 50 ml/min was maintained over the sample. Modulated temperature DSC was carried out using an underlying heating rate of 2° C./min and temperature modulation parameters of ±0.636° C. (amplitude) every 60 seconds (period). The instrument control software was Advantage for Q Series and Thermal Advantage and the data were analysed using Universal Analysis or TRIOS.

Reversed phase HPLC purity analysis was performed on an Agilent HP1loo series system equipped with a diode array detector and using ChemStation software.

| HPLC method for chemical purity determinations | |
|---|---|
| Parameter | Value |
| Type of method | Reversed phase with gradient elution |
| Sample Preparation | General: 0.5 mg/ml in acetonitrile: water 1:1 |

-continued

| HPLC method for chemical purity determinations | |
|---|---|
| | Forced degradation study: 0.2 & 0.5 mg/ml in various media |
| Column | Supelco Ascentis Express C18, 100 × 4.6 mm, 2.7 μm |
| Column Temperature (° C.) | 25 |
| Injection (μl) | 5 |
| Wavelength, Bandwidth (nm) | 255, 90 |
| Flow Rate (ml/min) | 2 |
| Phase A | 0.1% TFA in water |
| Phase B | 0.085% TFA in acetonitrile |

| Timetable | (min) | % Phase A | % Phase B |
|---|---|---|---|
| | 0 | 95 | 5 |
| | 6 | 5 | 95 |
| | 6.2 | 95 | 5 |
| | 8 | 95 | 5 |

Example 1: N-((1,2,3,5,6,7-hexahydro-s-indacen-4-yl)carbamoyl)-1-isopropyl-1H-pyrazole-3-sulfonamide monosodium monohydrate (Form 1)

N-((1,2,3,5,6,7-hexahydro-s-indacen-4-yl)carbamoyl)-1-isopropyl-1H-pyrazole-3-sulfonamide free acid was weighed into four vials (50 mg per vial). NaOH (1M in water) (see Table 3 for equivalents/volume added) and water (4 ml) were added to each of the sample vials. The conditions that these samples were subjected to are summarised in Table 3. The samples remained stirring in solution for 3 hours. Then it was attempted to remove the water by rotary evaporator, but after 3 hours the amount of water removed was very small. The solutions were then spread on glass slides to evaporate at room temperature. The solids formed were collected and analysed by XRPD, 1H-NMR, HPLC, IC and KF. IC and KF analysis confirmed formation of the monosodium salt, monohydrate. XRPD analysis confirmed formation of the Form 1 polymorph.

TABLE 3

| Example | Reaction conditions | HPLC purity |
|---|---|---|
| 1A | 1.1 eq. NaOH (142 μl) kept at RT | 97.1% |
| 1B | 1.0 eq. NaOH (129 μl) addition of base at 50° C., then cooling to 5° C. immediately | 96.8% |
| 1C | 1.0 eq. NaOH (129 μl) addition of base at 40° C., then cooling to 5° C. immediately | 96.7% |
| 1D | 1.0 eq. NaOH (129 μl) addition of base at 25° C. for 1 hour, then cooling to 5° C. | 96.7% |

Example 2: N-((1,2,3,5,6,7-hexahydro-s-indacen-4-yl)carbamoyl)-1-isopropyl-1H-pyrazole-3-sulfonamide monosodium monohydrate (Form 1)

N-((1,2,3,5,6,7-hexahydro-s-indacen-4-yl)carbamoyl)-1-isopropyl-1H-pyrazole-3-sulfonamide free acid (50 mg) was treated with a 9:1 (v:v) solvent mixture of acetone and water (0.5 ml). The resulting suspension was stirred at 25° C. before NaOEt (1.1 eq, 1M EtOH solution) was added. Further NaOEt solution was added until complete dissolution (total 1.3 eq NaOEt). t-Butyl methyl ether antisolvent (0.25 ml) was added to each sample prior to seeds of N-((1,2,3,5,6,7-hexahydro-s-indacen-4-yl)carbamoyl)-1-isopropyl-1H-pyrazole-3-sulfonamide monosodium monohydrate Form 1 polymorph (~2-4%). Further t-butyl methyl ether antisolvent was added to give a final solvent:antisolvent ratio of 1:3 (example 2A) and 1:5 (example 2B). The samples were then stirred at 25° C. for 2 hours prior to isolation of the solids through a PE frit. The samples were then stored under vacuum at room temperature for 18 hours followed by analysis by XRPD, $^1$H-NMR, HPLC, IC, KF, TGA and DSC.

TABLE 4

| Example | Final solvent:antisolvent ratio | Yield | HPLC purity |
|---|---|---|---|
| 2A | 1:3 | 34% | 98.1% |
| 2B | 1:5 | 85% | 97.6% |

Figure 2:
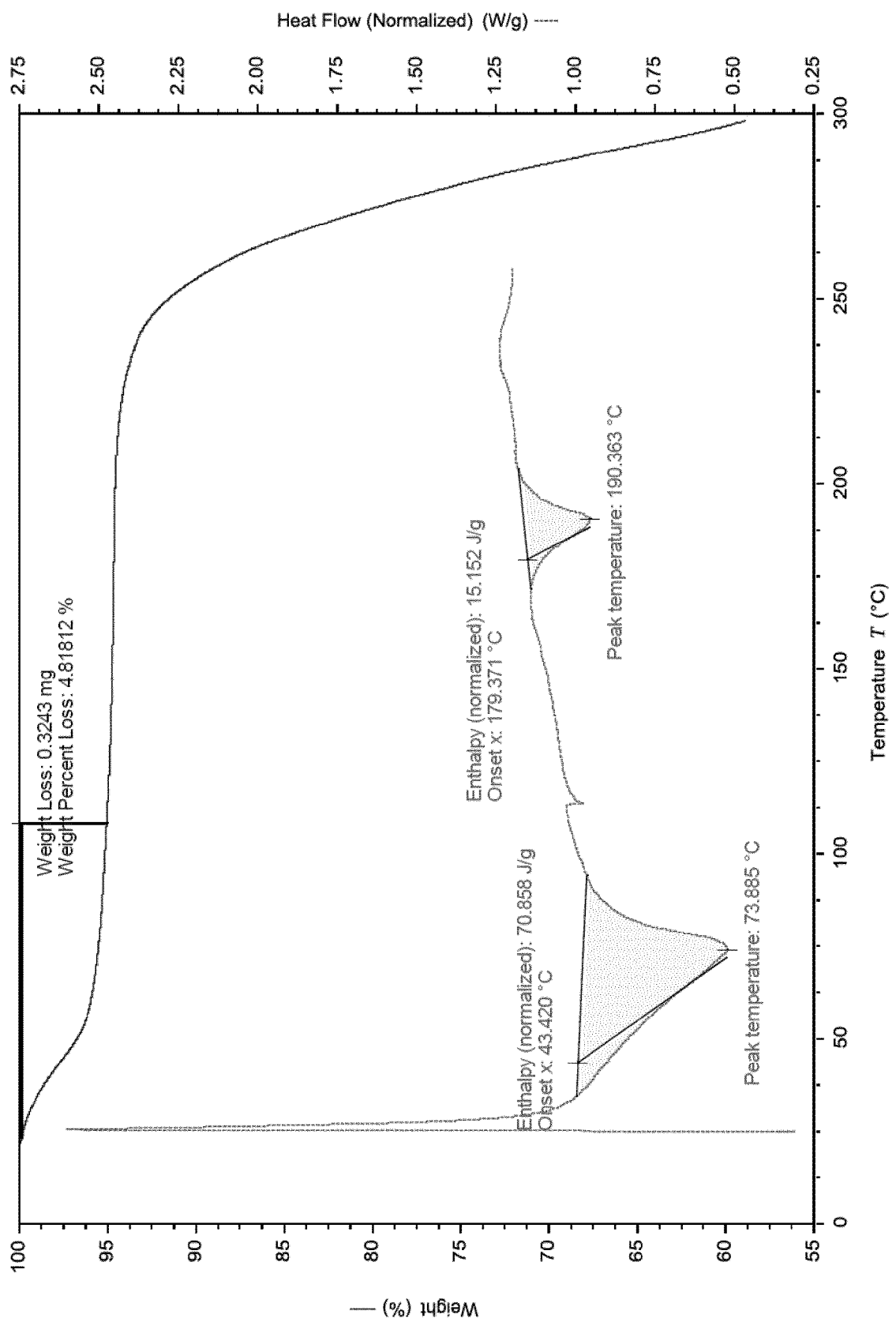
FIG. 2 shows TGA and DSC analysis of the salt of Example 2.

IC and KF analysis confirmed formation of the monosodium salt, monohydrate. XRPD analysis confirmed formation of the Form 1 polymorph. XRPD spectra are shown in FIG. 1. TGA and DSC spectra are shown in FIG. 2.

The XRPD spectra shown in FIG. 1 were obtained directly after preparation of the product, after storage for 1 week and for 5 weeks at 40° C. and 75% relative humidity, and after storage for 1 week and for 5 weeks at 25° C. and 97% relative humidity. The XRPD spectra shown in FIG. 1 indicate that the product obtained in Example 2 shows stability with respect to conversion into other polymorphic forms after storage at elevated temperature and humidity.

Example 3: N-((1,2,3,5,6,7-hexahydro-s-indacen-4-yl)carbamoyl)-1-isopropyl-1H-pyrazole-3-sulfonamide monosodium anhydrate (Form 2)

N-((1,2,3,5,6,7-hexahydro-s-indacen-4-yl)carbamoyl)-1-isopropyl-1H-pyrazole-3-sulfonamide monosodium salt (500 mg) was treated with a 10:1 (v:v) solvent mixture of isopropyl alcohol and H$_2$O (30 ml), and the reaction mixture was left stirring at 25° C. for 30 minutes. The resulting clear solution was then evaporated to produce a crystalline solid, which was analysed by XRPD, $^1$H-NMR, HPLC, IC, KF, TGA and DSC.

Figure 3:
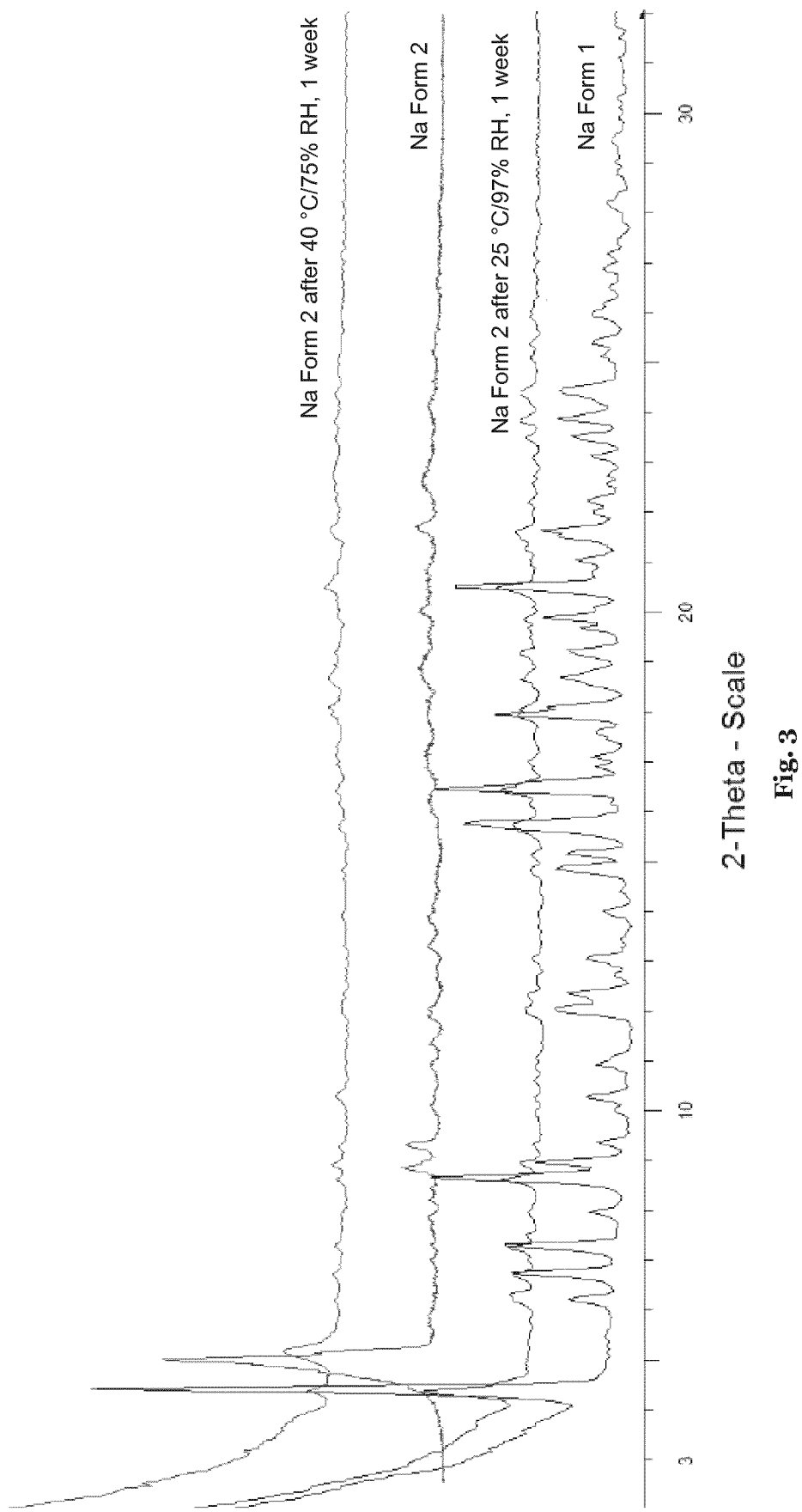
FIG. 3 shows XRPD analysis of the salt of Example 3.
Figure 4:
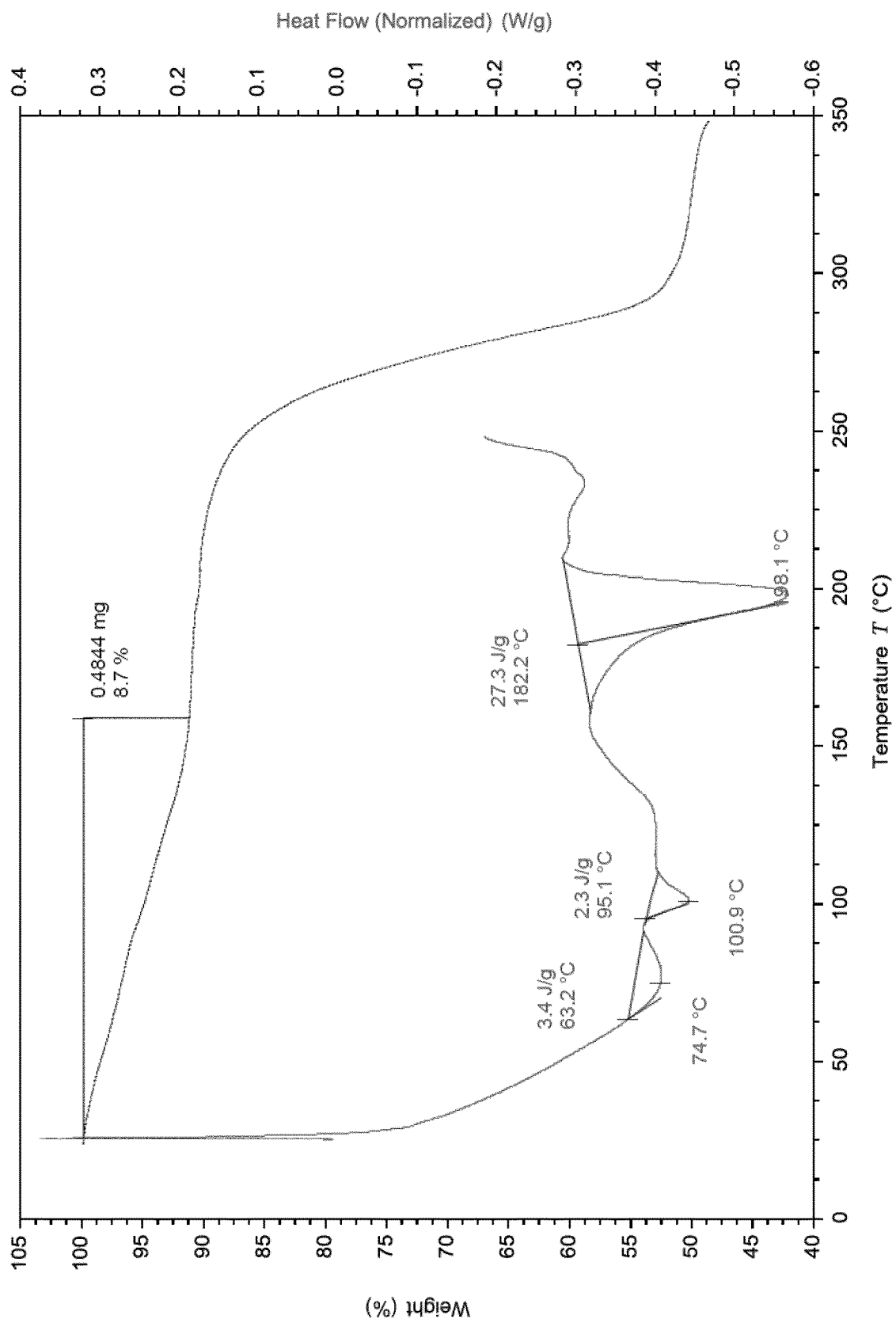
FIG. 4 shows TGA and DSC analysis of the salt of Example 3.

IC and KF analysis confirmed formation of the monosodium salt, anhydrate. The HPLC purity was 96.5%. XRPD analysis confirmed formation of the Form 2 polymorph. XRPD spectra are shown in FIG. 3. TGA and DSC spectra are shown in FIG. 4.

The XRPD spectra shown in FIG. 3 were obtained directly after preparation of the product, after storage for 1 week at 40° C. and 75% relative humidity, and after storage for 1 week at 25° C. and 97% relative humidity. FIG. 3 also shows the XRPD spectrum for Form 1 polymorph for reference. The XRPD spectra shown in FIG. 3 indicate that the monosodium anhydrate (Form 2) obtained in Example 3 is stable at elevated temperature (40° C.), and converts to the monosodium monohydrate (Form 1) at elevated humidity (97% RH).

Comparative Example 1: N-((1,2,3,5,6,7-hexahydro-s-indacen-4-yl)carbamoyl)-1-isopropyl-1H-pyrazole-3-sulfonamide free acid N-((1,2,3,5,6,7-hexahydro-s-indacen-4-yl)carbamoyl)-1-isopropyl-1H-pyrazole-3-sulfonamide free acid was prepared as described in WO 2016/131098 A1.

Comparative Example 2: N-((1,2,3,5,6,7-hexa-hydro-s-indacen-4-yl)carbamoyl)-1-isopropyl-1H-pyrazole-3-sulfonamide potassium salt N-((1,2,3,5,6,7-hexahydro-s-indacen-4-yl)carbamoyl)-1-isopropyl-1H-pyrazole-3-sulfonamide free acid (100 mg) was weighed out and KOH (1.1 eq, 1M aqueous solution, 283 µl) was added. Water was added and the reaction mixture was stirred at room temperature until a clear solution was obtained. The reaction mixture was left stirring for 2 hours, and then the water was removed by rotary evaporation overnight to produce a solid, which was analysed by XRPD, $^1$H-NMR, HPLC and IC.

IC analysis confirmed formation of the potassium salt. The HPLC purity was 96.3%. XRPD analysis revealed a fully amorphous material with no distinct diffraction peaks.

Attempts to convert the potassium salt into a crystalline substance by evaporation from acetonitrile or isopropyl alcohol were not successful, producing a gum in each case.

Evaluation Example 1

The sodium salt of Example 2 and the free acid of Comparative Example 1 were evaluated for solubility in water, stability in aqueous media and intrinsic dissolution rate. The results are set out in Table 5.

TABLE 5

| Analysis | Example 2 | Comparative Example 1 |
|---|---|---|
| Aqueous Solubility | 81 mg/ml | <0.5 mg/ml |
| Stability in aqueous media (24 hrs at room temperature) | No significant degradation | 37% degradation |
| Stability in aqueous media (24 hrs at 50° C.) | 2.7% degradation | 94% degradation |
| Intrinsic dissolution rate (at pH 2) | 10 µg/min · mm$^2$ | 4 µg/min · mm$^2$ |

The thermodynamic aqueous solubility was measured in water. The sodium salt was found to be soluble in water (81 mg/ml) with a resulting pH of 9.7. The free acid was found to be very poorly soluble in water (<0.5 mg/ml).

To measure the stability in aqueous media, the sodium salt was dissolved in water at a concentration of 0.2 mg/ml. Due to the very poor aqueous solubility of the free acid, the free acid was dissolved in a 1:1 mixture of water and acetonitrile at the same concentration of 0.2 mg/ml. Samples were kept at 50° C. in an amber vial and at room temperature in an amber vial as well as a clear vial. The sodium salt was found to be stable in aqueous media, whereas the free acid was found to be unstable.

The intrinsic dissolution rate was measured by the procedure set out in the US Pharmacopoeia, chapter 1087. The intrinsic dissolution rate of the sodium salt was found to be at least twice as high as that of the free acid.

The sodium salts of Examples 1, 2 and 3 have improved properties as compared to the free acid and potassium salt of Comparative Examples 1 and 2. These improved properties include crystallinity, aqueous solubility, intrinsic dissolution rate, stability under storage at elevated temperature and/or relative humidity, and stability in aqueous media.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A sodium salt of N-((1,2,3,5,6,7-hexahydro-s-indacen-4-yl)carbamoyl)-1-isopropyl-1H-pyrazole-3-sulfonamide.

2. The salt of claim 1, wherein the salt is a monosodium salt.

3. The salt of claim 1, wherein the salt is a monohydrate.

4. The salt of claim 1, wherein the salt is crystalline.

5. The salt of claim 1, wherein the salt is a crystalline monosodium salt of N-((1,2,3,5,6,7-hexahydro-s-indacen-4-yl)carbamoyl)-1-isopropyl-1H-pyrazole-3-sulfonamide monohydrate.

6. The salt of claim 1, wherein the salt is a solvate.

7. The salt of claim 1, wherein the salt is a hydrate.

8. A polymorphic form of the salt of claim 5, having an XRPD spectrum comprising peaks at approximately: 4.3° 2θ, 8.7° 2θ, and 20.6° 2θ.

9. A polymorphic form of the salt of claim 5, having an XRPD spectrum in which the 10 most intense peaks include 5 or more peaks which have an approximate 2θ value selected from: 4.3° 2θ, 6.2° 2θ, 6.7° 2θ, 7.3° 2θ, 8.7° 2θ, 9.0° 2θ, 12.1° 2θ, 15.8° 2θ, 16.5° 2θ, 18.0° 2θ, 18.1° 2θ, 20.6° 2θ, 21.6° 2θ, and 24.5° 2θ.

10. A pharmaceutical composition comprising a polymorphic form of claim 8, and a pharmaceutically acceptable excipient.

11. A process for preparing a sodium salt of N-((1,2,3,5,6,7-hexahydro-s-indacen-4-yl)carbamoyl)-1-isopropyl-1H-pyrazole-3-sulfonamide, comprising:
(a) contacting N-((1,2,3,5,6,7-hexahydro-s-indacen-4-yl)carbamoyl)-1-isopropyl-1H-pyrazole-3-sulfonamide free acid and a source of sodium ions in the presence of one or more polar solvents to form a mixture; and
(b) obtaining a solid sodium salt of N-((1,2,3,5,6,7-hexahydro-s-indacen-4-yl)carbamoyl)-1-isopropyl-1H-pyrazole-3-sulfonamide from the mixture.

12. A sodium salt of N-((1,2,3,5,6,7-hexahydro-s-indacen-4-yl)carbamoyl)-1-isopropyl-1H-pyrazole-3-sulfonamide obtainable by a process of claim 11.

13. The process of claim 11, wherein the one or more polar solvents used in step (a) comprise water and a polar aprotic organic solvent.

14. The process of claim 11, wherein the sodium salt of N-((1,2,3,5,6,7-hexahydro-s-indacen-4-yl)carbamoyl)-1-isopropyl-1H-pyrazole-3-sulfonamide is obtained in step (b) by addition of an antisolvent.

15. The process of claim 14, wherein the antisolvent is tert-butyl methyl ether.

16. The process of claim 13, wherein the polar aprotic organic solvent used in step (a) is acetone.

17. A process for preparing a crystalline monosodium salt of N-((1,2,3,5,6,7-hexahydro-s-indacen-4-yl)carbamoyl)-1-isopropyl-1H-pyrazole-3-sulfonamide monohydrate in the polymorphic form of claim 8, comprising:
(a) contacting N-((1,2,3,5,6,7-hexahydro-s-indacen-4-yl)carbamoyl)-1-isopropyl-1H-pyrazole-3-sulfonamide free acid and a source of sodium ions in the presence of water and optionally a polar aprotic organic solvent to form a solution; or dissolving N-((1,2,3,5,6,7-hexahydro-s-indacen-4-yl)carbamoyl)-1-isopropyl-1H-pyrazole-3-sulfonamide monosodium salt in a solvent mixture comprising water and optionally a polar aprotic organic solvent to form a solution; and
(b) obtaining the crystalline monosodium salt of N-((1,2,3,5,6,7-hexahydro-s-indacen-4-yl)carbamoyl)-1-isopropyl-1H-pyrazole-3-sulfonamide monohydrate in the polymorphic form from the solution.

18. The process of claim 17, wherein the polar aprotic organic solvent used in step (a) is acetone.

19. The process of claim 17, wherein the sodium salt of N-((1,2,3,5,6,7-hexahydro-s-indacen-4-yl)carbamoyl)-1-isopropyl-1H-pyrazole-3-sulfonamide is obtained in step (b) by addition of an antisolvent.

20. The process of claim 19, wherein the antisolvent is tert-butyl methyl ether.

21. A crystalline monosodium salt of N-(1,2,3,5,6,7-hexahydro-s-indacen-4-yl)carbamoyl)-1-isopropyl-1H-pyrazole-3-sulfonamide obtainable by a process of claim 17.

22. A pharmaceutical composition comprising a salt of claim 1, and a pharmaceutically acceptable excipient.

23. A method of ameliorating, palliating, delaying onset of, or reducing risk of a disease, disorder or condition in a subject, the method comprising the step of administering an effective amount of the salt of claim 1 to the subject, thereby ameliorating, palliating, delaying onset of, or reducing risk of the disease, disorder or condition, wherein the disease, disorder or condition is responsive to NLRP3 inhibition.

24. The method as claimed in claim 23, wherein the disease, disorder or condition is selected from:
    (i) inflammation;
    (ii) an auto-immune disease;
    (iii) cancer;
    (iv) an infection;
    (v) a central nervous system disease;
    (vi) a metabolic disease;
    (vii) a cardiovascular disease;
    (viii) a respiratory disease;
    (ix) a liver disease;
    (x) a renal disease;
    (xi) an ocular disease;
    (xii) a skin disease;
    (xiii) a lymphatic condition;
    (xiv) a psychological disorder;
    (xv) graft versus host disease;
    (xvi) allodynia;
    (xvii) any disease where an individual has been determined to carry a germline or somatic non-silent mutation in NLRP3;
    (xviii) cryopyrin-associated periodic syndromes (CAPS);
    (xix) Muckle-Wells syndrome (MWS);
    (xx) familial cold autoinflammatory syndrome (FCAS);
    (xxi) neonatal onset multisystem inflammatory disease (NOMID);
    (xxii) familial Mediterranean fever (FMF);
    (xxiii) pyogenic arthritis, pyoderma gangrenosum and acne syndrome (PAPA);
    (xxiv) hyperimmunoglobulinemia D and periodic fever syndrome (HIDS);
    (xxv) Tumour Necrosis Factor (TNF) Receptor-Associated Periodic Syndrome (TRAPS);
    (xxvi) systemic juvenile idiopathic arthritis;
    (xxvii) adult-onset Still's disease (AOSD);
    (xxviii) relapsing polychondritis;
    (xxix) Schnitzler's syndrome;
    (xxx) Sweet's syndrome;
    (xxxi) Behcet's disease;
    (xxxii) anti-synthetase syndrome;
    (xxxiii) deficiency of interleukin 1 receptor antagonist (DIRA); and
    (xxxiv) haploinsufficiency of A20 (HA20).

25. The method as claimed in claim 23, wherein the salt is administered as a pharmaceutical composition further comprising a pharmaceutically acceptable excipient.

26. A method of ameliorating, palliating, delaying onset of, or reducing risk of a disease, disorder or condition in a subject, the method comprising the step of administering an effective amount of the polymorphic form of claim 8 to the subject, thereby ameliorating, palliating, delaying onset of, or reducing risk of the disease, disorder or condition, wherein the disease, disorder or condition is responsive to NLRP3 inhibition.

27. The method as claimed in claim 26, wherein the disease, disorder or condition is selected from:
    (i) inflammation;
    (ii) an auto-immune disease;
    (iii) cancer;
    (iv) an infection;
    (v) a central nervous system disease;
    (vi) a metabolic disease;
    (vii) a cardiovascular disease;
    (viii) a respiratory disease;
    (ix) a liver disease;
    (x) a renal disease;
    (xi) an ocular disease;
    (xii) a skin disease;
    (xiii) a lymphatic condition;
    (xiv) a psychological disorder;
    (xv) graft versus host disease;
    (xvi) allodynia;
    (xvii) any disease where an individual has been determined to carry a germline or somatic non-silent mutation in NLRP3;
    (xviii) cryopyrin-associated periodic syndromes (CAPS);
    (xix) Muckle-Wells syndrome (MWS);
    (xx) familial cold autoinflammatory syndrome (FCAS);
    (xxi) neonatal onset multisystem inflammatory disease (NOMID);
    (xxii) familial Mediterranean fever (FMF);
    (xxiii) pyogenic arthritis, pyoderma gangrenosum and acne syndrome (PAPA);
    (xxiv) hyperimmunoglobulinemia D and periodic fever syndrome (HIDS);
    (xxv) Tumour Necrosis Factor (TNF) Receptor-Associated Periodic Syndrome (TRAPS);
    (xxvi) systemic juvenile idiopathic arthritis;
    (xxvii) adult-onset Still's disease (AOSD);
    (xxviii) relapsing polychondritis;
    (xxix) Schnitzler's syndrome;
    (xxx) Sweet's syndrome;
    (xxxi) Behcet's disease;
    (xxxii) anti-synthetase syndrome;
    (xxxiii) deficiency of interleukin 1 receptor antagonist (DIRA); and
    (xxxiv) haploinsufficiency of A20 (HA20).

28. The method as claimed in claim 26, wherein the polymorphic form is administered as a pharmaceutical composition further comprising a pharmaceutically acceptable excipient.

29. A method of inhibiting NLRP3 in a subject, comprising administering the salt of claim 1 to the subject thereby inhibiting NLRP3.

30. A method of analysing inhibition of NLRP3 or an effect of inhibition of NLRP3 by a salt, comprising contacting a cell or non-human animal with the salt of claim 1, and analysing inhibition of NLRP3 or an effect of inhibition of NLRP3 in the cell or non-human animal by the salt.

31. A method of inhibiting NLRP3 in a subject, comprising administering the polymorphic form of claim 8 to the subject thereby inhibiting NLRP3.

32. A method of analysing inhibition of NLRP3 or an effect of inhibition of NLRP3 by a polymorphic form, comprising contacting a cell or non-human animal with the polymorphic form of claim 8, and analysing inhibition of NLRP3 or an effect of inhibition of NLRP3 in the cell or non-human animal by the polymorphic form.

* * * * *